| United States Patent [19] | [11] Patent Number: 4,670,595 |
| Podder et al. | [45] Date of Patent: Jun. 2, 1987 |

[54] PROCESS FOR THE PRODUCTION OF 4-NITRODIPHENYLAMINES

[75] Inventors: Chiraranjan Podder, Dormagen; Harro Schlesmann, Odenthal, both of Fed. Rep. of Germany

[73] Assignee: Bayer Aktiengesellschaft, Leverkusen, Fed. Rep. of Germany

[21] Appl. No.: 825,216

[22] Filed: Feb. 3, 1986

[30] Foreign Application Priority Data

Feb. 9, 1985 [DE] Fed. Rep. of Germany ....... 3504479

[51] Int. Cl.$^4$ ............................................. C07C 85/04
[52] U.S. Cl. .................................................... 564/406
[58] Field of Search ........................................ 564/406

[56] References Cited

U.S. PATENT DOCUMENTS

| 3,435,074 | 3/1969 | Terao et al. | 564/406 |
| 4,209,463 | 6/1980 | Maender et al. | 564/406 |
| 4,404,400 | 9/1983 | Heise et al. | 564/406 |

*Primary Examiner*—Paul F. Shaver
*Attorney, Agent, or Firm*—Connolly and Hutz

[57] ABSTRACT

The reaction of 4-nitrohalogenbenzenes with primary aromatic amines in the presence of potassium carbonate and copper compounds to 4-nitrodiphenylamines gives better yield of purer products when synthetic polyamides are added.

5 Claims, No Drawings

PROCESS FOR THE PRODUCTION OF 4-NITRODIPHENYLAMINES

This invention relates to a process for the production of 4-nitrodiphenylamines by reaction of 4-nitrohalobenzenes with primary aromatic amines in the presence of potassium carbonate and copper compounds.

The reaction of halonitrobenzenes with aromatic amines is well known. Thus, it is known from DE-PS 185,663 that the reaction may be carried out in the presence of alkali metal carbonates and copper compounds as catalysts.

In addition, it is known that the extremely slow reaction may be accelerated by using potassium carbonate and removing the water produced by the reaction by azeotropic distillation. According to Example 1 of U.S. Pat. No. 2,927,943, moderately pure 4-nitrodiphenylamine was obtained in a yield of 73% of the theoretical yield after a reaction time of 21 hours under these conditions. In addition, it is known from U.S. Pat. No. 4,155,936 that, in the reaction of halonitrobenzenes with primary aromatic amines, the disadvantage of long reaction times is accompanied by contamination of the nitrodiphenylamines by formation of considerable quantities of tars and secondary products and also by the formation of nitrobenzene by reductive dehalogenation (c.f. U.S. Pat. No. 3,313,854, column 3, lines 64,65).

To overcome these disadvantages, it has been proposed to add co-catalysts, solubilizing agents and also dipolar aprotic solvents to the reaction mixture.

However, formanilide (U.S. Pat. No. 3,313,854), acetanilide (De-AS No. 1,518,307), salicylanilide (DE-AS No. 1,117,594) and ε-caprolactam (JP No. 8 122 751) show only a minimal effect.

The proposals made in U.S. Pat. No. 3,121,736 (addition of aminocarboxylic acids, alkyl diaminopolycarboxylic acids and salts thereof, disalicylaldiaminoalkanes, o-hydroxybenzalaminophenols, polyphosphates, carboxymethylmercaptosuccinic acid or Schiff's bases of salicylaldehydes), in JP-OS No. 8 240 445 (addition of benzyltrimethylammonium bromide, benzyltributyl phosphonium chloride, benzyltriphenyl phosphonium chloride, tetramethylammonium chloride, tetrabutyl phosphonium chloride) and in DE-OS No. 3,137,041 (addition of imidazole(ine), pyrimidine, bicyclic amidine, triazine, phenanthroline, dipyridine, bis-quinolone) lead to problems at the working-up stage.

Although the use of caesium compounds in accordance with DE-OS No. 3,246,151 gives an improved yield, the compounds add considerably to the cost of the process.

The addition of polyethers differing in structure as described in U.S. Pat. No. 4,155,936, JP-OS No. 80 100 342 and JP-OS No. 82 02 243 does not produce improvement either.

Other additions, which unfortunately produce no improvement, are described in U.S. Pat. No. 3,055,940 (dimethyl formamide and hexamethylphosphoric acid triamide), U.S. Pat. No. 3,277,175 (dimethyl sulphoxide), DE-OS No. 2,633,811 (N-methyl pyrrolidone) and JP-OS No. 71/09452 (dimethyl formamide).

A process for the production of 4-nitrodiphenylamines corresponding to the following general formula:

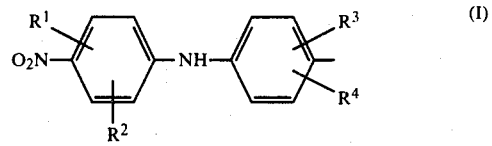

wherein $R^1$, $R^2$, $R^3$ and $R^4$, which may be the same or different, represent hydrogen or a $C_1$–$C_9$ alkyl radical; by reaction of halonitrobenzenes corresponding to the following general formula:

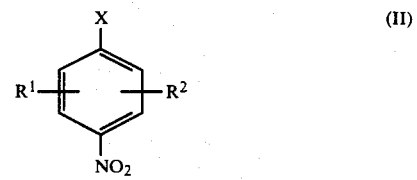

wherein
X represents chlorine or bromine; and
$R^1$ and $R^2$ are as defined above;
with primary aromatic amines corresponding to the following general formula:

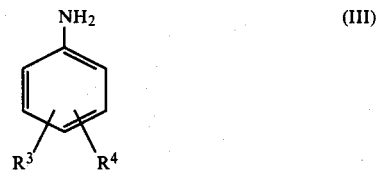

wherein $R^3$ and $R^4$ are as defined above; in the presence of potassium carbonate and copper compounds has now been found and is characterized in that synthetic polyamides are added.

Alkyl radicals $R_1$ to $R_4$ preferably contain from 1 to 3 carbon atoms.

Suitable halonitrobenzenes are, for example, 4-nitrochlorobenzene, 4-nitrobromobenzene, 4-nitro-2-methylchlorobenzene.

Suitable primary aromatic amines are, for example, aniline, o-toluidine, m-toluidine, p-toluidine, 4-ethyl aniline, 4-butyl aniline, 4-isopropyl aniline, 3,5-dimethylaniline and 2,4-dimethyl aniline.

The aromatic amines may, of course, also be used in the form of mixtures more especially isomer mixtures. In general from 1 to 6 moles of the aromatic amine are used per mole of halonitrobenzene.

In a preferred embodiment 3 to 5 mol of amine are used per mol of halonitrobenzene whereof 1.2 to 2 mole of amine are added prior to the beginning of the reaction and the remainder is added during the reaction at such a rate that the molar excess of amine in reaction to halonitrobenzene constantly amounts to 100 to 400%.

The process is preferably used for the production of 4-nitrodiphenylamine from 4-nitrochlorobenzene and aniline.

Examples of copper catalysts suitable for use in the process according to the present invention are copper(I) iodide, copper(I) chloride, copper(II) chloride, copper(I) bromide, copper(II) bromide, copper(I) cyanide, copper(I) oxide, copper(II) oxide, copper(II) carbonate, basic copper(II) carbonate, copper(II) sulphate, copper(II) nitrate, copper(II) formate, copper(II) acetate and organic and inorganic coordination compounds of monovalent or divalent copper. Oxygen-containing copper compounds, such as copper(II) oxide, copper(II) carbonate, basic copper(II) carbonate or copper(I) oxide, are preferably used. The copper catalyst is generally used in a quantity of from 0.001 to 0.1 mole, preferably from 0.01 to 0.05 mole, per mole of halonitrobenzene used. The copper catalysts may be used individually or in admixture with one another.

Suitable synthetic polyamides are polyaddition products of lactams or polycondensation products of ω-aminocarboxylic acids containing at least 4 carbon atoms or of dicarboxylic acids with diamines, for example polyamide-6, polyamide-11, polyamide-12, polyamide-66, polyamide-610, polyamide-61, polyamide-63T and mixtures thereof. Of the synthetic polyamides, polyamide-6, polyamide-66 and polyamide 610 are preferably used.

The polyamides are generally used in such quantity that from 0.01 to 0.1 mole of -CONH-groups are present per mole of halonitrobenzene.

Rubidium and Caesium compounds may in addition be added in catalytic quantities to the reaction mixture.

The potassium carbonate may be used in an equivalent quantity or in an excess of up to 1.5 times the equivalent quantity.

The water formed during the reaction is advantageously removed from the reaction mixture by distillation using an entraining agent. Suitable entraining agents are, for example, xylene, toluene, benzene, chlorobenzene or chlorotoluene.

If necessary, the process according to the present invention may be carried out in the presence of additional diluents, for example inert hydrocarbons, such as xylene, in order to adjust or maintain the reaction temperature range. In addition, the aromatic primary amines themselves may be used for this purpose.

The reaction temperatures in the process according to the present invention may vary within wide ranges. In general, they are from 140° to 225° C., preferably from 180° to 210° C.

The process according to the present invention may be carried out continuously or in batches in known manner.

The reaction mixture may likewise be worked-up by different methods. The salts present in the reaction mixture may be physically separated off at elevated temperature by centrifugation or filtration. Washing with warm xylene, following by drying, leaves a light gray, powder-form product.

Xylene, unreacted halonitrobenzene, primary aromatic amine and solvent may be completed separated off from the filtrate in a rotary evaporator or in a tubular-coil evaporator under a vacuum of from 5 to 50 mbar and at a temperature of from 150° to 220° C., the nitrodiphenylamines accumulating in the form of a melt which in turn solidifies on cooling. The mixture obtained as distillate may be used without further treatment for the next batch. Another method is partially to distill the filtrate in vacuo and largely to separate the nitrodiphenylamines by crystallization. The nitrodiphenylamines accumulate in highly pure form and may thus be directly further processed. The distillate from the vacuum distillation and the mother liquor from crystallization may be reused.

In another embodiment, water is added to the reaction mixture, the potassium salts are dissolved and copper oxide and polyamides are separated off by filtration. Xylene, unreacted p-nitrochlorobenzene and primary amine may be removed from the filtrate by steam distillation. In this case, the nitrodiphenylamine accumulates in the form of a granulate which may be used for further processing.

The copper catalyst and the polyamide may be repeatedly used. A quantity of catalyst and co-catalyst smaller than the quantity originally used may optionally be added to them in fresh form to maintain full activity.

Highly pure 4-nitrodiphenylamines may be obtained in high yields and short reaction times using the process acording to the present invention. Virtually no secondary products are formed in the process according to the invention.

The 4-nitrodiphenylamines produced by the process according to the present invention may readily be reduced to amino-diphenylamines in known manner and as such are valuable intermediate products for the producition of, for example, dyes or stabilizers for rubber (c.f. U.S. Pat. No. 3,163,616).

EXAMPLE 1

157.6 g of p-nitrochlorobenzene, 186 g of aniline, 100 g of potassium carbonate, 20 ml of xylene, 2 g of copper oxide and 2.5 g of polyamide-6 having a solution viscosity of 3.1 (1 g in 100 ml of cresol at 20° C.) were introduced into a 1 liter flask equipped with a stirrer and column with water separator.

The reaction mixture was heated, with stirring, to 195° C. The content of the flask was then maintained at that temperature, while a further quantity of aniline (ca. 186 g) were added portionwise, until from 10.5 to 11 ml of water had separated off. The content of 4-chloronitrobenzene was determined from a sample by liquid chromatography. If it was below 1.5% of the original quantity, the reaction was terminated by cooling, but otherwise was continued until that level was reached. The total reaction time was from 9 to 10 hours.

250 ml of water were then added to the reaction mixture which, thereafter, was filtered at 90° C. and the volatile components removed by steam distillation. The aqueous phase of the flask contents was separated off, the organic phase solidified on cooling. 213.5 g of a yellow granular substance were obtained which, according to liquid chromatographic analysis, contained 88.7%, by weight, of 4-nitrodiphenylamine, corresponding to a yield of 88.4%, based on 4-nitrochlorobenzene.

Further tests produced the following results:

| Example | Additive | Solution viscosity ($\eta$) | Quantity added (g) | Reaction time (h) | 4-nitrodiphenyl amine content (%, by weight) | Yield of crude 4-nitrodiphenyl amine (g) | Yield (% of th.) |
|---|---|---|---|---|---|---|---|
| 2 | Polyamide 11 | 2.4 | 5.0 | 12 | 86.3 | 213.5 | 86.0 |
| 3 | Polyamide 12 | 2.5 | 5.0 | 11 | 87.6 | 213.8 | 87.4 |
| 4 | Polyamide 66 | 2.5 | 2.5 | 12 | 87.2 | 212.1 | 86.3 |
| 5 | Polyamide 610 | 2.2 | 5.0 | 10.5 | 87.4 | 214.4 | 87.5 |
| 6 | Polyamide 63T | 2.6[1] | 2.5 | 11 | 88.3 | 212.8 | 87.7 |

-continued

| Example | Additive | Solution viscosity ($\eta$) | Quantity added (g) | Reaction time (h) | 4-nitrodiphenyl amine content (%, by weight) | Yield of crude 4-nitrodiphenyl amine (g) | Yield (% of th.) |
|---|---|---|---|---|---|---|---|
| 7 | Polyamide 6 | 2.5 | 2.5 | 9.5 | 88.5 | 213.8 | 88.3 |
| 8 | Polyamide 11 | 2.4 | 2.5 | 13 | 87.4 | 212.1 | 86.5 |
| 9 | Polyamide 66 | 2.5 | 2.5 | 10.5 | 88.0 | 212.7 | 87.4 |
| 10 | Polyamide 63T | 2.6[(1)] | 5.0 | 12 | 88.0 | 213.1 | 87.5 |

[(1)] 1 g in 100 ml 95% by weight $H_2SO_4$ at 20° C.

We claim:
1. A process for the production of 4-nitrodiphenylamines corresponding to the following general formula:

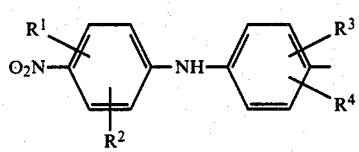 (I)

wherein
$R^1$, $R^2$, $R^3$ and $R^4$, which may be the same or different, represent hydrogen or a $C_1$-$C_9$ alkyl radical: by reaction of halonitrobenzenes corresponding to the following general formula:

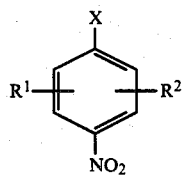 (II)

wherein
X represents chlorine or bromine; and
$R^1$ and $R^2$ are as defined above; with primary aromatic amines corresponding to the following general formula:

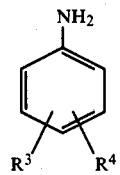 (III)

wherein
$R^3$ and $R^4$ are as defined above; in the presence of potassium carbonate and copper compounds, characterized in that synthetic polyamides are added.
2. A process as claimed in claim 1, characterized in that $R_1$, $R_2$, $R_3$ and $R_4$ represent hydrogen.
3. A process as claimed in claim 1, characterized in that the polyamides are used in such a quantity that from 0.01 to 0.1 mole of —CONH-groups are present per mole of halonitrobenzene.
4. A process as claimed in claim 1, characterized in that polyamide-6, polyamide-66 or polyamide-610 is used as the polyamide.
5. A process as claimed in claim 1, characterized in that 3 to 5 mol of amine are used per mol of halonitrobenzene whereof 1.2 to 2 mol are added prior to the beginning of the reaction and the remainder is added during the reaction at such a rate that the molar excess of amine in relation ot halonitrobenzene constantly amounts to 100 to 400%.

* * * * *